United States Patent [19]

Lepp et al.

[11] 4,049,499

[45] Sept. 20, 1977

[54] MICROBIAL MEDIUM HAVING FLUORESCENT GROWTH INDICATOR

[75] Inventors: Cyrus A. Lepp; Robert D. Mason, both of Painted Post; William S. Ramsey, Corning, all of N.Y.

[73] Assignee: Corning Glass Works, Corning, N.Y.

[21] Appl. No.: 701,894

[22] Filed: July 1, 1976

[51] Int. Cl.$^2$ .......................... C12K 1/06; C12K 1/10
[52] U.S. Cl. ............................. 195/100; 195/103.5 M
[58] Field of Search ........................... 195/99–103.5 M

[56] References Cited
PUBLICATIONS

Chemical Abstracts, vol. 75, 59948s; 1971.
Chemical Abstracts, vol. 74, 1456t; 1971.
Chemical Abstracts, vol. 75, 137373s; 1971.
Pedersen and Lode, Arch. Mikrobiol, vol. 77, pp. 118–126; 1971.

*Primary Examiner*—Lionel M. Shapiro
*Assistant Examiner*—Robert J. Warden
*Attorney, Agent, or Firm*—James A. Giblin; Clinton S. Janes, Jr.; Clarence R. Patty, Jr.

[57] ABSTRACT

Solidified, polar, micorbial growth medium containing 8-anilino-1-naphthalenesulfonic acid or a salt thereof. Microbial colonies grown on the medium can be detected fluorimetrically.

9 Claims, 5 Drawing Figures

MICROBIAL MEDIUM HAVING FLUORESCENT GROWTH INDICATOR

RELATED PATENT APPLICATION

Patent applications Ser. No. 701,891, "Medium and Method for Distinguishing *Neisseria gonorrhoeae* and *Neisseria meningitidis*", filed in the names of L. B. Simpson and M. M. Takeguchi, the application filed of even date and assigned to the same assignee as this application.

BACKGROUND OF THE INVENTION

1. Field:

This disclosure is concerned generally with microbial growth media and specifically with media which include chemical growth indicators.

2. Prior Art:

Colonies of microorganisms grown on solidified or gel-like media are commonly located, examined, and counted using visible light which is transmitted through the media. This procedure becomes difficult under conditions in which the colonies are very small or transparent and in cases where the growth medium is opaque, highly colored, or very irregular. For example, if chocolate or milk agar is the growth medium, or if any medium is used on a wood or paper surface, it can be difficult to detect and study microbial colonies with transmitted light.

It is known that microorganism such as *Pseudomonas fluorescens* and *Streptomyces fluorescens* produce naturally fluorescent pigments and such microbes can be easily recognized by their fluorescence. It is also known that anionic or cationic fluorescent materials can be incorporated into growth media for the purpose of labeling individual bacteria. However, some of the anionic and cationic fluorescent materials have the disadvantages of being inhibitory to some microorganisms or they may react with particular components of some media.

The substance 8-anilino-1-naphthalenesulfonic acid (ANS) has been used as a fluorescent probe in studying the interaction of a suspension of *Escherichia coli* and colicins. We are unaware, however, of the use of that material in a solidified, gel-like microbial growth media. Surprisingly, we have found that the incorporation of a small amount of ANS, or a salt thereof, into such media, makes possible the fluorimetric detection of microbial colonies. Hence, the problems associated with the use of transmitted light (e.g. opacity or translucency) are avoided. A detailed description of the growth medium is described below.

SUMMARY OF THE INVENTION

The microbial growth medium of this disclosure comprises a semi-solid, gel-like, polar, micorbial growth material having incorporated therein a quantity of 8-anilino-1-naphthalenesulfonic acid (ANS) or a salt thereof. In especially useful embodiments, the growth material is an opaque or translucent gel (e.g. chocolate or milk agar) or a substantially transparent medium carried on a translucent or opaque support. In another useful embodiment, the medium is used to detect substantially transparent and/or very small colonies of microbes. The ANS or salt thereof is included in the growth material in a quantity sufficient to permit the visual or fluoroimetric detection of microbial colonies grown thereon.

SPECIFIC EMBODIMENTS

Figure 1:
FIG. 1 is a photograph showing (with long wave length u.v. light) the growth of colonies of *Escherichia coli* in agar without (left) and with (right) ANS incorporated into the agar (at 0.08 mg/ml), after three days incubation at 30° C.
Figure 2:
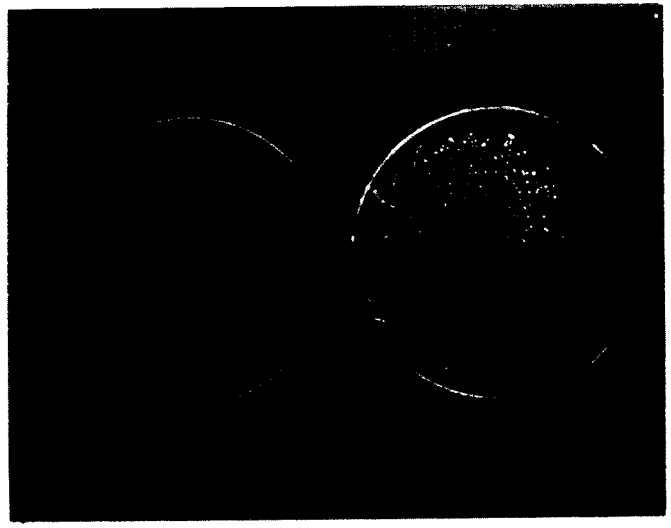
FIG. 2 is a photograph (with long wave length u.v. light) of colonies of *E. coli* incubated overnight at 37° C. on chocalate agar without (left) and with (right) the ANS (at 0.08 mg/ml).
Figure 3:
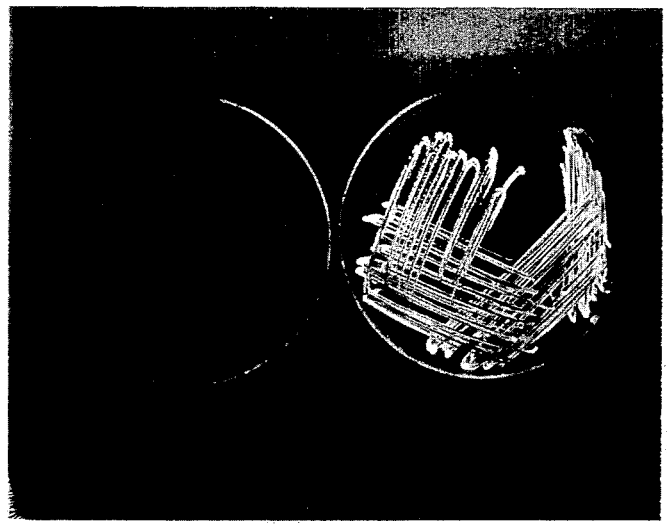
FIG. 3 is a photograph of similarily compared colonies of *Serratia marcescens* grown on the medium used for FIG. 2.
Figure 4:
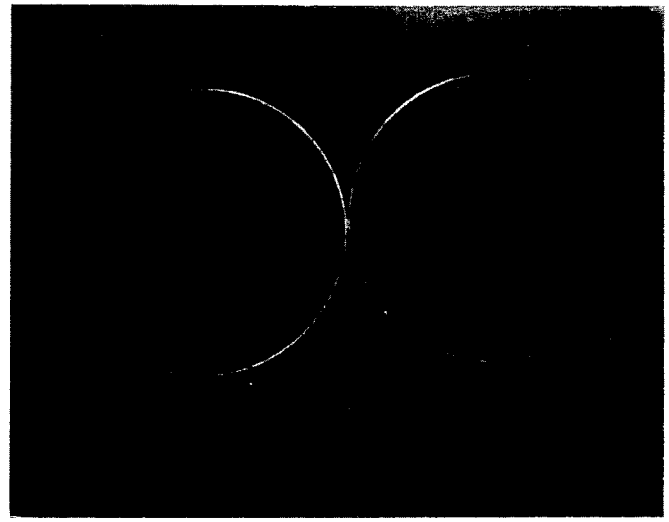
FIG. 4 similarly compares colonies of *Staphylococcus aureus* grown on the medium used for FIG. 2.

To appreciate better the significance of our initial observations, a variety of fluorogenic compounds were incorporated at 0.08 mg/ml (unless noted otherwise) in nutrient media, streaked with *Escherichia coli* and *Staphylcoccus aureus*, incubated overnight, and examined for fluorescence.

With the following compounds, no fluorescent colonies resulted:

4-amino-1-naphthol hydrochloride
Lissamine Rhodamine B Sulfonyl Chloride
Auramine O
7-anilino-1-napthol-3-sulfonic acid (saturated solution)
7-hydroxy-2-naphthalenesulfonic acid, sodium salt
5-fluorescein isothiocyanate
Dansyl chloride 5-dimethyl aminonaphthalene-1-sulfonyl chloride Rose Bengal
6-p-toluidino-2-naphthalenesulfonyl chloride Although the following compounds did allow some growth of fluorescent colonies, the best fluorescence was observed with the indicated ANS salts:

8-anilino-1-naphthalenesulfonic acid, sodium salt
8-anilino-1-naphthalenesulfonic acid, magnesium salt
Acridine orange
Pyrenebutyric acid
6-p-toluidino-2-naphthalene sulfonic acid
Fluorescamine (Fluram TM)

ANS ($C_6H_5NHC_{10}H_6SO_3H$), or salts thereof (e.g. sodium, magnesium, potassium, ammonium, etc.), and similar fluorogenic compounds such as 8-p-toluidino-1- and 6-p-toluidino-2-naphthalene sulfonic acids are not significantly fluorescent in a polar environment such as an aqueous gel because polar compounds such as water tend to quench any fluorescence. In a non-polar or hydrophobic environment, however, the compounds will readily and visibly fluoresce when appropriately stimulated. We have found that when microbes are grown in a polar micorbial growth medium containing ANS or a salt thereof, the location of the colonies can be easily recognized visually or fluorimetrically since the colonies, in taking up the ANS, provide a hydrophobic environment in which fluorescence is enhanced. Since the microbes (or at least portions of the surfaces of the microbes) provide a hydrophobic or non-polar environment for the ANS, and thus minimize quenching of fluorescence, it can be appreciated that the ANS or salt thereof can be used to locate colonies of all microbes. Accordingly, it is intended that the expressions microbe, microbial, or all reasonable equivalents include, but are not limited to, bacteria, fungi, yeasts, protozoans and other unicellular organisms regardless of whether they form true colonies. The expression polar, or its equivalent, refers to a substance or compound having a pair of equal and opposite charges (e.g., water or various hydrophilic materials). The expression incubating conditions, or its equivalent, refers to those growth conditions recognized as being conducive to microbial growth.

The ANS may be in acid form or, more conveniently, in the form of a salt (e.g. magnesium or sodium salt) as described below. The concentration of ANS (or salt) in the growth medium need only be sufficient to permit conveniently detectable fluorescence of the microbes. Although most of the experiments were done with a concentration of ANS equal to about 0.08 mg per ml of medium (e.g. agar), it can be appreciated that the amount of ANS used can vary. Varying the concentration of ANS from 0.02 to 0.16 mg/ml did not appear to inhibit the growth of the microbes described below. It should be noted, however, that in copending patent application Ser. No. 701,891, "Medium and Method for Distinguishing *Neisseria gonorrhoeae* and *Neisseria meningitidis*", it was found that ANS at certain critical minimum concentrations in media specific to meningococci and gonococci bacteria appeared to inhibit the growth of the *N. gonorrhoeae* and not the N. meningitidis, thereby providing a method of distinguishing the two species. Thus, even though the ANS used in the media of this disclosure did not appear to inhibit the growth of the organisms studied, in certain limited applications concerned with specific media (e.g. Thayer-Martin) there did appear to be some inhibition of gonococci above a minimum concentration (mg/ml) which depended on the medium used.

Our invention is illustrated in more detail in the examples below. Unless otherwise indicated, all techniques used were conventional.

EXAMPLES

The 8-anilino-1-naphthalenesulfonic acid in the form of a magnesium salt was obtained commercially (Eastman) and is herein referred to as ANS. The ANS at a level of 0.08 mg/ml of nutrient growth medium was added to Nutrient Agar (Difco) or to chocolate agar prepared by adding hemoglobin (Difco) at a final concentration of 0.01 g/ml to gonococcus (GC) Medium (Difco). The media were sterilized, poured into petri plates, and allowed to solidify to a gel. These plates, along with control plates not containing ANS, were separately innoculated with the bacteria *Escherichia coli, Serratia marcescens, Staphylococcus aureus,* and *Bacillus subtilis*. The Nutrient Agar plates were incubated at 30° C. and the chocolate agar plates at 37° C. overnight and then examined.

Figure 5:
FIG. 5 shows the fluorescent colonies of *Bacillus subtilis* grown on the medium used for FIG. 2. (Only chocolate Agar plus 0.08 mg/ml ANS).

In every case tested, the growth on the plates with ANS was at least about equal to growth in the absence of the compound. When both the Nutrient Agar and the chocolate agar plates were examined with long wave length u.v. light (340 to 380 nm, peak at 366 nm), only the colonies on media containing the ANS fluoresced with a bluish-white light. The highest amount of fluorescence was shown by the colonies of *S. Marcescens* and *E. coli,* followed by *S. aureus* and *B. subtilis*. Actual photographs comparing four results are shown in FIGS. 1–4. FIG. 5 shows only the fluorescent colonies of the *B. Subilis*. Both individual colonies and areas of heavy growth were observed to fluoresce, on both the translucent Nutrient Agar and the opaque chocolate agar.

Further evidence of the lack of deleterious effects of the ANS on the growth of the bacteria studied was obtained by innoculation of dublicate 250 ml flasks with 20 ml Nutrient Broth (Difco) or 20 ml Nutrient Broth containing 0.02, 0.08, or 0.16 mg/ml ANS with 0.5 ml of an *E. coli* culture in Nutrient Broth at a turbidity of 200 klett units. The flasks were incubated at 37° C. with shaking and the turbidity determined periodically using a Klett-Summerson colorimeter. There was no inhibition of growth by ANS.

Inasmuch as the above-described media are subject to various modifications given this disclosure, it is intended that the above examples should be construed as illustrative only and that the scope of the disclosed invention should be limited only by the following claims.

We claim:

1. A microbial growth medium comprising a semi-solid, gel-like, polar material having incorporated therein 8-anilino-1-naphthalene sulfonic acid or a salt thereof in a quantity sufficient to permit the fluorimetric detection of microbial growth.

2. The medium of claim 1 wherein the polar material comprises an agar.

3. The medium of claim 2 wherein the agar is chocolate agar.

4. The medium of claim 1 wherein the amount of anilinonaphthalene sulfonic acid or salt thereof ranges from about 0.02 to 0.16 mg per ml of medium.

5. In a microbial growth medium comprising a microbial nutrient material selected from agar and chocolate agar, the improvement which comprises the addition of an amount of 8-anilino-1-naphthalenesulfonic acid or a salt thereof in a quantity sufficient to permit the fluorimetric detection of microbial growth thereon.

6. A method of detecting the presence of microbes in a sample, the method comprising the steps of:
A. incubating at least a portion of the sample with a microbial growth medium comprising a gel-like, polar material containing 8-anilino-1-naphthalenesulfonic acid or a salt thereof; and
B. examining the microbial growth medium for fluorescence.

7. The method of claim 6 wherein the gel-like material is agar or chocolate agar.

8. The method of claim 6 wherein the examination of step (B) is accomplished by exposing the material to u.v. light having a wave length ranging from about 340 to 380 nm.

9. The method of claim 6 wherein the amount of anilinonaphthalenesulfonic acid, or salt thereof in the medium ranges from about 0.02 to 0.16 mg per ml of medium.

* * * * *